United States Patent [19]
Lord et al.

[11] Patent Number: 5,622,838
[45] Date of Patent: Apr. 22, 1997

[54] DNA PREPARATION CODING FOR RICIN A AND METHODS OF USING SAME

[75] Inventors: John M. Lord; Lynne M. Roberts, both of Leamington Spa; Francis I. Lamb, Kenilworth, all of England

[73] Assignee: Imperial Chemical Industries PLC, Great Britain

[21] Appl. No.: 327,434

[22] Filed: Mar. 23, 1989

Related U.S. Application Data

[63] Continuation of Ser. No. 630,815, Jul. 13, 1984, abandoned.

[30] Foreign Application Priority Data

Jul. 15, 1983 [GB] United Kingdom ............... 8319265
Mar. 13, 1984 [GB] United Kingdom ............... 8406569

[51] Int. Cl.$^6$ .............................. C12N 1/21; C12N 5/10; C12N 15/29; C12P 21/02
[52] U.S. Cl. ............... 435/69.1; 435/252.3; 435/252.31; 435/252.33; 435/252.35; 435/254.11; 435/254.21; 435/325; 435/418; 435/419; 536/23.6
[58] Field of Search ................... 435/320, 172.3, 435/69.1, 252.3, 68.1, 240.2, 240.4, 252.31, 252.33, 252.35, 254.11, 254.21; 536/23.1, 23.6

[56] References Cited

U.S. PATENT DOCUMENTS 4,578,355  3/1986  Rosenberg ........................ 435/317

OTHER PUBLICATIONS

Funatsu, G. et al. 1979. Agric. Biol. Chem 43:2221.
Goeddel, D. et al. 1980. Nature 287:411.
Butterworth, A. and J.M. Lord. 1983. Eur. J. Biochem 137:57.
Roberts et al. (1981) *Eur. J. Biochem.* vol. 119 pp. 31–41.
Suggs et al. (1981) *Proc. Nat'l. Acad. Sci. USA* vol. 78 pp. 6613–6614.
Ragg et al. (1977) Biochim. Biophys. Acta, vol. 474, pp. 226–233.
Wahl et al. (1987) Methods in Enzymology, vol. 152, pp. 399–407.
Maniatis et al. (1981) Molecular Cloning (Cold Spring Harbor Laboratory, Cold Spring Harbor, N.Y.) pp. 324–325 & 344–349.

*Primary Examiner*—Mindy Fleisher
*Assistant Examiner*—Philip W. Carter
*Attorney, Agent, or Firm*—Banner & Witcoff, Ltd.

[57] ABSTRACT

A DNA preparation is provided which comprises a nucleotide sequence coding for at least a portion of the precursor polypeptide of ricin. Also provided are recombinant DNA molecules containing such a nucleotide sequence, as well as microorganisms transformed with such recombinant DNA molecules.

15 Claims, 1 Drawing Sheet

DNA PREPARATION CODING FOR RICIN A AND METHODS OF USING SAME

This application is a continuation of application Ser. No. 630,815, filed Jul. 13, 1984, now abandoned.

BACKGROUND OF THE INVENTION

This invention relates to DNA comprising a nucleotide sequence coding for at least a portion of a polypeptide which is a plant toxin of the ricin type, as hereinafter defined. It also relates to recombinant DNA molecules comprising a DNA sequence which codes for a polypeptide which is or is closely related to a natural plant toxin of the ricin type. Ricin, and also other plant toxins such as abrin, modeccin and viscumin, consist of two polypeptide chains (known as the A and B chains) linked by a disulphide bridge, one chain (the A chain) being primarily responsible for the cytotoxic and the other chain (the B chain) having sites enabling the molecule to bind to cell surfaces. Ricin is produced in the plant *Ricinis communis* (also known as the castor bean plant) via a precursor protein known as "preproricin".

Preproricin comprises a single polypeptide chain which includes a leader sequence. The leader sequence is subsequently removed in the organism to give proricin which is then cleaved to eliminate a linker region and joined by a disulphide bond to form the mature protein. The toxicity of ricin-type toxins operates in three phases: (1) binding to the cell surface via the B chain; (2) penetration of at least the A chain into the cytosol, and (3) inhibition of protein synthesis through the A chain attacking the 60S subunits of the ribosomes. Thus, separated A and B chains are essentially non-toxic, the inherently toxic A chain lacking the ability to bind to cell surfaces in the absence of the B chain.

It is also known that in ricin-type toxins the B chain binds to cell surfaces by virtue of galactose recognition sites, which react with glycoproteins or glycolipids exposed at the cell surface.

It has already been suggested that the toxicity of the ricin A chain might be exploited in anti-tumour therapy, by replacing the indiscriminately-binding B chain with a different carrier component having the ability to bind only to tumour cells. Thus, various immunotoxins have already been prepared, consisting of a conjugate of whole ricin or a separated natural ricin A chain and a tumour-specific monoclonal antibody. Although these known conjugates are of considerable potential in themselves, there is scope for improvement.

One problem with the known conjugates arises from a structural feature of the A chain from natural ricin. It is known that the natural ricin A chain becomes N-glycosylated during its synthesis, by enzymes present in Ricinus cells, and it is thought that the resulting sugar moieties are capable of non-specific interactions with cell surfaces. Thus, it appears that the known A chain conjugates are capable of a certain amount of binding with non target cells, even in the absence of the natural B chain, thus increasing the toxicity of such immunotoxins towards non target cells.

Another problem with the known ricin A chain conjugates stems from the fact that the B chain seems to have an important secondary function in that it somehow assists in the intoxication process, apart from its primary function in binding the ricin molecule to the cell surfaces. This secondary function is lost if the B chain is replaced by a different carrier component such as a monoclonal antibody.

If it were possible to prevent interactions between the cell surface via the A chain sugar moieties, whilst preserving the secondary toxicity-increasing function of the B chain, the toxicity of a whole ricin antibody conjugate towards normal cells could be reduced, and towards target cells could be increased, thus improving the therapeutic index of the immunotoxin. It is also known that the natural ricin B chain is N-glycosylated and the B chain sugar moieties may also contribute to non specific interactions, Also, the sugar moieties in both chains enable the ricin molecule to be sequestrated by reticuloendothelial cells in the liver, and so would lead to the rapid excretion from the system of a drug based on a part or the whole of the ricin molecule in which such sugar moieties were still present.

Attempts to remove all the sugar moieties from natural ricin by chemical or enzymatic methods have so far failed. Nevertheless the major obstacle confronting the use of known whole ricin-antibody conjugates is the presence of two galactose binding sites in the ricin B chain. These B chain galactose binding sites are primarily responsible for the non-specific cellular interactions of current whole ricin-antibody conjugates, particularly when used in vivo. Their presence in the natural toxin clearly eliminates or reduces the targeting specificity conferred by the antibody.

An improved immunotoxin based on ricin or another plant toxin of the ricin type, not suffering from these problems, could consist of a whole toxin molecule modified so that it is not N-glycosylated, and so that the B chain has no galactose recognition sites, but retains its secondary intoxication-promoting properties, coupled to a carrier moiety which delivers the toxin to the target cells. This could be a tumour-specific or cell/tissue specific vehicle such as a suitable monoclonal antibody.

Our research which has so far been concentrated on ricin itself, has indicated that the assembly of ricin (and the related agglutinin which consists of two ricin-like molecules with slightly modified A and B chains) does not involve the separate synthesis of the A and B chains as the products of distinct mRNA's, but rather the initial formation of a single polypeptide precursor containing both the A chain and B chain sequences. This is thought to apply in the case of other toxins of the same type.

SUMMARY OF THE INVENTION

This invention is based on the idea of preparing a genetically-engineered microorganism capable of expressing a molecule of a toxin of the ricin type, as defined above, or alternatively part of such a toxin molecule, or a precursor of such a molecule (which could be converted to the toxin molecule itself) which toxin molecule could be modified as suggested above and could be used to construct an effective toxin conjugate by combining it with a tumour-specific or cell/tissue specific monoclonal antibody or other carrier moiety, such as a hormone or lectin.

The fact that ricin is formed via a precursor polypeptide will enable a cell system to be constructed by known techniques which expresses a ricin precursor. The ricin precursor product could then be chemically or enzymatically converted to the desired modified ricin. An analagous technique could be used in the case of other ricin-type toxins as herein defined. An alternative technique would be to divide from the DNA sequence that codes for the precursor two sequences which code separately for the A and B chains, to insert these separated sequences into different cloning vehicles and to insert the resulting recombinant DNA molecules into separate host microorganisms. One such host would then express the A chain polypeptide sequence and the other the B chain polypeptide sequence. These sequences could then be combined to form the desired modified ricin molecule. This technique could obviously also be used for any ricin-type toxins in which the A and B chains are encoded by distinct mRNA gene pools. This latter approach would be preferred on safety grounds, in that separate and therefore non-toxic A and B chains would be expressed.

BRIEF DESCRIPTION OF THE DRAWING

The drawing summarizes the preparation of a transformed host containing a DNA sequence which codes for the ricin A and B chain precursor polypeptide.

DESCRIPTION OF THE PREFERRED EMBODIMENTS

According to one aspect of the invention we provide a biologically pure and homogeneous sample of DNA comprising a nucleotide sequence coding for at least a portion of a precursor of a ricin-type toxin polypeptide, or mutants thereof.

Said portion preferably comprises the A chain or the B chain of the mature protein.

More specifically, we provide a sample of DNA including at least a substantial portion of any of the following DNA sequences, which sample is biologically-pure: nucleotides −72 to 1623, or nucleotides −72 to 801, or nucleotides 838 to 1623, as defined hereinafter at Table 1 or at least a portion of a nucleotide sequence which is equivalent thereto by virtue of degeneracy of the genetic code.

According to another aspect of this invention we provide a recombinant DNA molecule comprising a DNA sequence which codes for a polypeptide sequence present in a plant toxin of the ricin type, as defined herein.

More specifically, we provide a recombinant DNA molecule containing a DNA sequence which codes for a A and B chain precursor polypeptide of a plant toxin of the ricin type.

Alternatively, we provide a recombinant DNA molecule containing a DNA sequence coding for at least a portion of either the A chain or the B chain of a plant toxin of the ricin type.

According to a further aspect of the present invention we provide a genetically modified host microorganism which contains a recombinant DNA molecule as hereinbefore defined.

In the recombinant DNA molecules according to the present invention, the nucleotide sequence coding for the B chain may be modified to eliminate or inactivate the galactose binding sites, and the precursor polypeptide and hence in the mature protein, to eliminate or inactivate the galactose binding sites, and the sequences encoding the signals for N-glycosylation may also be modified to render them ineffective or to eliminate them. Examples of techniques which may prove useful are deletion or oligonucleotide mediated mutagenesis.

The host organism may be a plant cell or an animal cell or preferably a microorganism.

The microorganism may be a prokaryote or a eukaryote. As examples of prokaryotes may be mentioned Gram-negative bacteria, e.g. *E. coli, Methylophilus methylotrophus* and *Alcaligenes eutrophus*; and Gram-positive bacteria, e.g. *Streptomyces, Bacillus subtilis* and Arthrobacter. As examples of eukaryotes may be mentioned yeasts, for examples *Saccharomyces cerevisiae.*

The recombinant DNA molecules may comprise a cloning vector such as a plasmid or phage vector into which has been inserted the DNA sequence coding for at least a portion of a precursor polypeptide, or at least a portion of either the A chain or the B chain, of a ricin-type plant toxin.

The cloning vector is preferably a plasmid although we do not exclude the possibility that it may be a phage vector. The plasmid may be a naturally-occurring plasmid or preferably a composite derived from fragments of other plasmids. Where a composite plasmid is employed it preferably contains promoter sequences which improve expression of the ricin gene.

Examples of suitable plasmids which may be used as cloning vehicles are inter alia for Gram-negative bacteria: pBR322, pAT153, pUC8, pGSS15 and pMB9; and for *S. cerevisiae*: pMA91, pMA230, YRp7, and YEp6. The vector will be selected to be suitable for the particular host envisaged.

We also provide a method of obtaining a recombinant DNA molecule which comprises preparing a double-stranded DNA sequence which codes for a polypeptide sequence present in a plant toxin of the ricin type and inserting said double-stranded DNA sequence into a cloning vector.

More specifically such a method may comprise isolating the mRNA which codes for the ricin A and B chain precursor polypeptide, synthesising single-stranded cDNA from said mRNA using reverse transcriptase and a suitable primer, assembling the second DNA strand onto the template formed by said first strand by means of DNA polymerase followed by S1 nuclease, and inserting the resulting double-stranded cDNA into a cloning vector.

Alternatively, the cDNA assembled from the mRNA may be cut into separate portions which code respectively for separate portions of the ricin molecule, for example for the A and B chains, which portions are then inserted into separate cloning vectors.

As stated above the cloning vector is preferably a plasmid such as pBR322, pAT153, of pUC8, and this may be cut open by means of the restriction endonuclease Pst I, and may be tailed with oligo (dG), and annealed with the double-stranded cDNA which has been tailed with oligo (dC).

We also provide a method of producing a modified transformed host by introducing into a suitable host microorganism a recombinant DNA molecule according to this invention.

The microorganism used as the host for cloning is preferably a Gram-negative bacterium and more preferably *E. coli.*

After cloning, the DNA sequence coding for the ricin precursor (or the precursor of another ricin-type toxin which is formed from a precursor) may be removed from the host cloning vector. It may then be divided into two portions which code for separate regions of the toxin molecule, for example the A and B chains, these portions introduced into separate second cloning vectors and new hosts modified with each of the resulting new recombinant DNA molecules. Alternatively it may be introduced while into a second cloning vector. The second cloning vectors comprise suitable promoter sequences and the position and direction of insertion of the whole coding sequence or portion thereof into the second cloning vector are such that on introducing the new recombinant DNA molecules into suitable host microorganisms, e.g. *E. coli* or *S. cerevisiae*, expression of the desired gene sequence is obtained.

Figure 1:
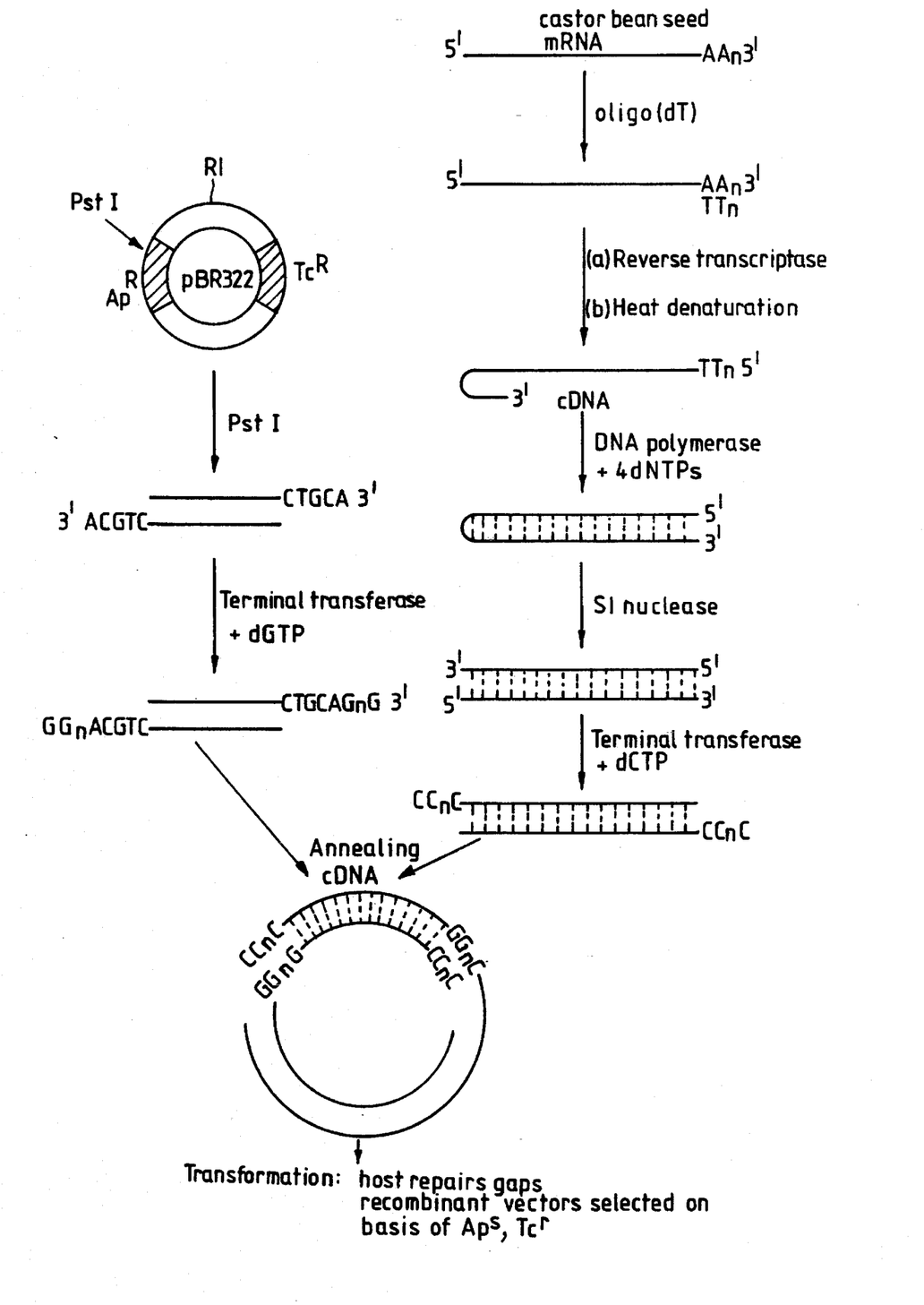

The preparation of a transformed host containing a DNA sequence which codes for the ricin A and B chain precursor polypeptide will now be described by way of example, first in general terms and then in detail. This process is summarised in the accompanying diagram.

Firstly, the mRNA encoding this precursor was enriched in known manner by sucrose density gradient centrifugation. The corresponding cDNA was assembled in single-strand form onto this mRNA in known manner using the enzyme reverse transcriptase, a growing point having first been provided on the mRNA using oligo (dT) as primer which binds onto the polyadenylated 3'-terminus of the mRNA. The immediate product of this reaction is a DNA-RNA hybrid. The RNA strand is removed by hydrolysis, leaving the single-strand DNA intact. This is converted to the double stranded form using the enzyme DNA polymerase in the presence of free nucleotides, which results in a hairpin-shaped molecule, the curved end of which is then removed by the single-strand specific nuclease S1. The resulting double strand cDNA is then tailed with oligo (dC) using terminal transferase, size fractionated to remove small molecules, or vice versa and annealed with the pBR322 or pAT153 vector which has been cut open with Pst I and tailed with oligo (dG) using terminal transferase, the cytosine tails on the DNA base pairing with the guanine tails on the vector.

The resulting chimaeric plasmids containing the DNA segment coding for the ricin precursor polypeptide were then used to transform *E-coli* DH1 cells, and the presence of the chimaeric plasmid was ensured by selecting cells displaying tetracycline resistance and ampicillin sensitivity. Over 1600 $Tet^r$, $Amp^s$ clones were obtained. Colonies derived from each clone were transferred to nitrocellulose filters and clones containing the desired DNA sequence identified using a 32P-end labelled 20 mer oligonucleotide probe, having the DNA sequence

```
         A  C  A  A
ACCTACAA TT TT CT CC
         G  T  G  G
``` which hybridises to DNA containing the complementary sequence

```
         T  G  T  T
TGGATGTT AA AA GA GG.
         C  A  C  C
```

As the ricin precursor polypeptide has been found to contain the amino sequence—Trp-Met-Phe-Lys-Asn-Asp-Gly— the DNA sequence responsible for this is deduced using the genetic code to be the latter mentioned above.

Using appropriate hybridisation and wash conditions, e.g. as described by Singer-Sam et al in (1983) Proc. Natl. Acad. Sci. (U.S.A.), Vol. 80 pp 802–806, 80 clones were selected as positively containing the desired DNA sequence, and of these, the eight largest in the plasmid pBR322 have been initially chosen for further characterisation. Their relationship to the castor bean lectin precursor polypeptides has been confirmed using the hybrid release translation assay. Of the eight clones mentioned above, four, respectively with 1614, 1950, 1059 and 1020 base pairs, have been selected for sequencing.

In detail, the transformed host was prepared as follows:

A. cDNA Synthesis 1. mRNA Extraction and Fractionation

100–200 g of ripening Ricinus seeds were frozen and ground to a powder in liquid nitrogen, and homogenised in a Waring blender for 1–2 minutes in 50 mM tris-HCl pH 9, 150 mM NaCl, 5 mM EDTA and 5% SDS. The homogenate was extracted with an equal volume of phenol:chloroform (1:1) and the phases were separated by centrifugation. The organic phase and residue were reextracted with 0.5 volume of 20 mM tris-HCl pH 9.0, 2 mM EDTA and the resulted aqueous phase was combined with the original one. The total aqueous phase was reextracted repeatedly with equal volumes of phenol:chloroform until no material was present at the interface. RNA was precipitated by the addition of 2 volumes of cold ethanol after making the solution 200 mM in NaCl.

After overnight precipitation at −20° C. The RNA was centrifuged at 10,000 rpm for 30 minutes in an MSE 18 or MSE 21 centrifuge; the pellet was then washed repeatedly in 3M NaAc pH 5.5 until no polysaccharide was detectable in the supernatant by ethanol precipitation. The final pellet was dissolved in 300 mM NaCl and precipitated as above.

mRNA molecules bearing poly(A) tails were extracted by affinity chromatography on oligo(dT)-cellulose: after hybridisation at room temperature for 30 min. in 400 mM NaCl, 20 mM tris-HCl pH 7.6, 0.2% SDS, the beads were pelleted and washed three times in the above buffer and two times in 200 mM NaCl, 20 mM tris-HCl pH 7.6, 0.1% SDS. The slurry was poured into a column and washed further with the last buffer until the $A_{260}$ of the eluate reached the background level. Poly(A)-containing RNA was then eluted with 20 mM tris-HCl pH 7.6 at 50° C. The eluate was monitored with an ISCO continuous flow UV cell. Poly(A)-containing RNA was precipitated overnight from 200 mM NaCl by the addition of 2 volumes of cold ethanol at −20° C. and was then washed three times with 70% ethanol, and redissolved in 10 mM tris-HCl pH 7.0 to approximately 1 μg/μl.

The mRNA was heated for 2 min. at 65° C. and quench cooled. Approximately 400 μg of $poly(A)^+$ RNA was layered on top of a 10–30% ribonuclease-free sucrose (Sigma) density gradient in 100 mM tris-HCl pH 7.5, 0.5% SDS, 1 mM EDTA, and centrifuged in a Beckman L5-65B centrifuge using an SW27 rotor at 25,000 rpm at 17° C. for 14 hours. 400 μl fractions were collected with an ISCO density gradient fractionator using the continuous flow UV cell.

Each fraction was made 200 mM in NaCl and precipitated with 2 volumes of cold ethanol by freeze-thawing in liquid nitrogen three times, and recovered by centrifugation in an Eppendorf microcentrifuge for 30 minutes at 4° C., washed once with 70% ethanol, and redissolved in 10 μl of 10 mM tris-HCl pH 7.0. An aliquot from each fraction (1 μl) was translated in a reticulocyte lysate cell free system and the lectin precursor immunoprecipitated to identify the fraction enriched for lectin mRNA.

2. First Stand Synthesis

Fractionated $poly(A)^+$ RNA was reverse transcribed at 0.5 μg/μl in the presence of 50 mM tris-HCl pH 8.3, 10 mM $MgCl_2$, 100 mM KCl, 1 mM of dATP, dTTP and dGTP, 250 μM dCTP, 0.06 μg/μl oligo $(dT)_{12-18}$, 10 mM DTT and 0.4 units/μl of reverse transcriptase from avian myeloblastosis virus. (3H)dCTP or α-($^{32}$P)dCTP were included in the reaction as appropriate.

The reaction mixture was incubated at 42° C. for 45 minutes, at which point an equal volume of 5 mM tris-HCl pH 8.3, 5 mM DTT, 250 μM dCTP was added along with the same amount of enzyme as previously. The reaction was incubated for a further 45 minutes at 45° C. and terminated by freezing. Aliquots were analysed on 1% denaturing agarose gels along with the products of the second strand and $S_1$ nuclease reactions.

3. Second Strand Synthesis mRNA-cDNA hybrids were denatured by boiling the first strand reaction for 3 minutes and cooling rapidly. After pelleting insoluble material in the Eppendorf microfuge for 2 minutes the supernatant was transferred to a fresh chilled tube. For the standard reaction, reagents were added as follows, ignoring elements already present: dATP, dGTP and dTTP to 100 µM, Hepes-KOH pH 6.9 to 105 mM, KCl to 92 mM, dCTP, labelled as appropriate, to 80 µM, and 0.1 units/µl of DNA polymerase. The reaction was allowed to proceed at 20° C. for 6 hours, at which time cDNA was removed from the mixture by gel filtration on 1 ml columns of Bio-Gel P60 in 10 mM tris-HCl pH 7.6, 20 mM NaCl, 1 mM EDTA. Fractions were monitored by Cerenkov or liquid scintillation counting, and peak excluded fractions were pooled and precipitated from 0.3M NaAc pH 6 by the addition of 2 volumes of cold ethanol. Precipitates were recovered by centrifugation in the Eppendorf microcentrifuge for 30 minutes in the cold, and dissolved in water to about 2.5 µg/µl of RNA—equivalent material.

4. $S_1$ Nuclease Digestion

Single-stranded regions of double-stranded cDNA were digested with $S_1$ nuclease from *Aspergillus oryzae*, in the presence of 300 mM NaCl, 30 mM NaAc pH 4.5, 3 mM $ZnCl_2$. The reaction was incubated for 15 minutes at 37° C. and then for 15 minutes at 15° C., and was terminated by the addition of tris-HCl pH 7.6 to 130 mM and EDTA to 10 mM; it was then extracted with an equal volume of phenol:chloroform:isoamyl alcohol (25:24:1) and precipitated from 300 mM NaAc pH 6 with 2 volumes of cold ethanol. The precipitate was dissolved in 10 mM tris-HCl pH 8, 0.1 mM EDTA to 0.25 µg/µl RNA equivalent.

5. Addition of Homopolymer Tails to DNA

Double-stranded DNA was tailed using terminal transferase with dCTP at 0.001–0.01 µg/µl in the presence of 140 mM potassium cacodylate pH 7.6, 30 mM tris base, 0.1 mM DTT, 1 mM $CoCl_2$ and ($^3H$) or ($^{32}P$)-labeled dCTP in 75–150 fold excess over 3' termini. The reaction was carried out at 37° C. for 6 minutes. The extent of incorporation of label was followed by assaying the amount of TCA—insoluble radioactivity as a proportion of the total radioactivity, counting in Bray's scintillant.

The reaction was stopped by chilling and adding EDTA to 10 mM, after which unincorporated material was removed by gel filtration as described. Tailed cDNA was precipitated as before, and dissolved in 1M NaAc pH 8, 10 mM tris-acetate pH 8, 1 mM EDTA ready for fractionation.

PstI-cleaved pBR322 DNA was similarly treated, except that dGTP replaced dCTP.

6. Fractionation of Tailed cDNA cDNA was fractionated on 5–20% linear sucrose density gradients in 1M NaAc pH 8, 10 mM tris-acetate pH 8, 1 mM EDTA, and centrifuged overnight at 39,000 rpm in an SW50.1 rotor. DNA sedimentation was checked on a parallel gradient loaded with a mixture of HinfI and PstI digests of pBR322 DNA, and fractions of this gradient were run on a 1% neutral agarose gel. Fractions from the cDNA gradient were diluted with an equal volume of water and precipitated with 2 volumes of cold ethanol, and then pooled to give three final fractions, a large cDNA fraction (larger than 2,200 bp), an intermediate fraction (1,000–2,200 bp) and a fraction containing smaller cDNAs (600–1,000 bp). cDNA molecules smaller than 600 bp were discarded.

The three final fractions were dissolved to approximately 5 ng/µl in 150 mM RbCl, 10 mM tris-HCl pH 7.6, 0.2 mM EDTA.

B. Annealing and Transformation

1. Annealing dC-tailed cDNA was mixed with dG-tailed pBR322 or pAT153 in approximately equimolar quantities, at a concentration of 0.4 ng/µl of vector. Buffers were as described above. The mixtures were heated to 70° C. for 30 minutes and then cooled overnight to room temperature, and slowly chilled to 4° C. Competent cells were added and transformed as described below.

2. Preparation of Competent Cells and Transformation

DH1 cells$^x$ were grown in 10 ml cultures of psi broth (2% tryptone, 0.5% yeast extract, 10 mM NaCl, 20 mM $MgCl_2$, pH adjusted to 7.6 with KOH; all bacteriological reagents from Difco), and grown at 37° C. in a shaking waterbath to $A_{550}$=0.3. 1 ml of this was then inoculated into 25 ml of the F.$^-$, end A1, hsd R17 ($r_k-$, $m_k-$), supE 44, thi-1, lambda$^-$, recA1, gyr A96, rel A1? same medium and grown to $A_{550}$=0.48. The cells were then chilled on ice for 15 minutes and harvested at 5,000 rpm for 5 minutes in an MSE 21 centrifuge at 4° C. They were then resuspended in 10 ml of 100 mM RbCl, 50 mM $McCl_2$, 10 mM $CaCl_2$, 35 mM NaAc pH 5.8, 15% glycerol and kept on ice for 15 minutes.

The cells were again harvested, and resuspended in 1 ml of 10 mM RbCl, 75 mM $CaCl_2$, 10 mM MOPS-KOH pH 5.8, 15% glycerol, and kept on ice for a further 15 minutes.

100 µl of the cells thus prepared were mixed with the annealed DNA samples, and incubated on ice for 30 minutes, after which they were heat-shocked at 42° C. for 90–120 seconds. 1 ml of psi broth was added, and the cells were grown at 37° C. for 1 hour. They were then centrifuged briefly, and resuspended in 100 µl of psi broth and plate on LB plates containing 14 µg/ml tetracycline (LB is 1% tryptone, 0.5% yeast extract, 170 mM NaCl, 1.5% agar).

After 18–24 hours growth at 37° C., colonies were counted and spotted onto LB plates containing 33 µg/ml ampicillin to identify those transformants containing recircularised or uncut plasmids. Over 1600 Tet$^r$ Amp$^s$ clones were picked and transferred in ordered arrays onto large plates of LB containing 14 µg/ml tetracycline.

C. Screening

1. Labelling of Oligonucleotide

The ricin B chain specific oligomer (20 mer) was end labelled using polynucleotide kinase. 500 ng of oligonucleotide was incubated in 50 mM tris pH 8.5, 10 mM $MgCl_2$, 5 mM DTT, 0.1 mM spermidine-HCl, 0.1 mM EDTA with 60 µCi δ($^{32}p$) ATP and 1 µl polynucleotide kinase (Boehringer) for 35 min at 37° C. The reaction was stopped by adding an equal volume of 0.6M $NH_4AC$ and the bulk of non incorporated δATP was removed by passage through a sephadex G25 column in 0.14M NaCl, 0.02M tris pH 7.6, 0.005M EDTA, 0.1% SDS. The probe was stored frozen at −20° C.

2. Colony Hybridization Using Oligonucleotide Probe

Transformants were grown on nitrocellulose filters (Schleicher & Schuell 0.45µ) layered over LB plus tetracycline. The filters, in triplicate, were then transferred to LB-Tet plates containing 200 µg/ml chloramphenicol for 16 h at 37°. The filters were placed colony side up on two sheets of 3 mm paper wetted with 0.5M NaOH for 15 mins at room temperature. The same procedure was followed for the following two washes (1) with 1M tris pH 8.0, and (2) with 1M tris pH 8, 1.5M NaCl (30 mins). The filters were air dried and baked at 80° C.

Prehybridizations and hybridizations were done in double sealed polythene bags. The filters were prehybridized in 0.9M NaCl, 0.09M tris 7.4, 0.006M EDTA, 0.5% NP40, 2× Denhardts, 0.2% SDS, 100 µg/ml denatured single strand salmon sperm DNA and 70 µg/ml tRNA. Prehybridization was done for 4 h at 55° C. The prehybridization buffer was then squeezed from the bag and fresh buffer added that contained 50 ng labelled probe (to give a maximum concentration of 5 ng/ml buffer). Annealing was done overnight at 37° C.

Non stringent washes were done with 6× SSC at room temperature. The filters were washed in 4 changes of 6× SSC over 3 h. The triplicate filters were then washed at three different temperatures determined from the base composition and degree of mismatch of the probe. Using 2° C. for every A or T and 4° C. for every C or G in the probe the wash temperatures selected were 52° C., 56° C. and 60° C. The filters were washed at the stringent temperature in 6× SSC for 10 minutes and then dried thoroughly. The filters were exposed to X-ray film overnight.

D. Hybrid Selection Procedure

1. DNA Binding

Plasmid DNA was purified from the positive clone(s) and 10–15 µg linearized with EcoRl. After phenol:chloroform extraction and ethanol precipitation the pellet was dissolved in 0.5 ml 0.1× SSC. 0.5 ml 1M NaOH was then added and the mixture allowed to stand for 15 mins at room temperature. 4 ml of a prechilled neutralizing solution (1.5M NaCl, 0.25M HCl, 0.25M tris-Cl pH 8.0) was added and the 5 ml DNA sample sucked by vacuum through swinnies containing wetted Schleicher and Schuell 0.45µ filter discs. 5 ml 6× SSC was then passed through the filter(s). These were air dried and then baked for 2 h at 80° C.

2. Hybrid Selection Protocol

The filter(s) were placed in 5 ml bottles and prehybridized for 4 h at 41° C. in 50% formamide, 0.4M NaCl, 10 mM pipes-NaOH pH 6.4, 4 mM EDTA, 0.5 µg/ml tRNA, 10 µg/ml poly(A). The buffer was removed and the filter(s) typically hybridized overnight at 41° C. in 50% formamide buffer (above) containing approx. 20 µg poly (A)$^+$ RNA from castor beans. The buffer was removed and the filters washed twice for 15 mins in each of the following: (1) 1× SSC, 0.5% SDS at room temperature, (2) 0.1× SSC, 0.1% SDS at room temperature, (3) 0.1× SSC, 0.1% SDS at 50° C., (4) 0.1× SSC, 0.1% SDS at room temperature. The filters were drained and 200 ul hybrid release buffer (90% formamide, 10 mM pipes-NaOH pH 6.4, 1 mM EDTA, 0.5% SDS) added to each and mixed for 30 mins at 40° C. The buffer was removed into a fresh eppendorf and NaCl added to 0.2M. The released mRNA was precipitated with ethanol, rinsed several times in 70% ethanol, dried and dissolved in 5 µl sterile water. The sample was translated in a reticulocyte lysate cell free system and the products run out directly on an SDS-polyacrylamide gel or firstly immunoprecipitated with appropriate antisera.

The DNA sequence coding for the above-mentioned ricin precursor polypeptide of two of the above-mentioned clones, referred to herein as pBRCL 6 and pBRCL 17 (RCL=*Ricinus communis* lectin) has now been determined by a combination of the Sanger dideoxy method (Sanger et al, 1977—Proc. Natl. Acad. Sci. U.S.A. 74, 5463–67) and the procedure of Maxam and Gilbert (Maxam and Gilbert, 1980—Meth. Enzym. 65, 499–560). In order to determine the sequence at the ends of each insert the inserts were excised from pBR322 and Pst I and ligated into Pst I linearized, phosphatased plasmid pUC8 (Vierra and Messing, 1982—Gene 19, 259–268). *E. Coli* DHI cells were transformed by these recombinant plasmids. These new recombinant plasmids are referred to herein as pRCL6 and pRCL17.

It is apparent that the two inserts contain a region of common sequence and that together they represent a total ricin precursor sequence. There are no nucleotide differences between the overlapping regions of the inserts in pRCL6 and pRCL17.

A new recombinant DNA molecule was then constructed that contains the complete nucleotide sequence encoding the ricin precursor polypeptide. This was achieved by isolating a fragment, 323 base pairs in length, obtained from pRCL17 by digestion with the restriction endonuclease Sau 961, and ligating this fragment to a fragment 1561 base pairs in length isolated after a partial digestion of pRCL6 with Sau 961 Ligation was performed in 50 mM tris HCl (pH 7.4) 10 mM MgCl$_2$, 10 mM dithiothreitol, 1 mM spermidine, 10 mM ATP, 0.1 mg/ml BSA with 5 units commercial T4 DNA ligase, and incubation proceeded overnight at 15° C. After a standard phenol/chloroform extraction and ethanol precipitation the ligated DNA was pelleted, dissolved in a small volume of 10 mM tris HCl (pH 7.4), 1 mM EDTA and digested to completion with Pst I. The resulting linearised DNA was then ligated (as above) with an equal quantity of Pst I linearised, phosphatased pUC8. The new recombinant DNA molecule containing the entire DNA sequence of the ricin precursor and referred to as pRCL617, was used in conventional manner to transform *E. coli* DHI cells.

The nucleotide sequence of pRCL617 is shown hereinafter.

This sequence was deduced from the two overlapping cDNA inserts in clones pRCL6 and pRCL17 (the limits of the DNA inserts in each of these two clones are given below).

Nucleotide residues are numbered in the 5' to 3' direction with the first residue of the codon specifying the amino terminal residue of mature ricin A chain numbered 1 and the nucleotides on the 5' side of reside 1 indicated by negative numbers. The 5' terminal sequence does not extend to the 5' end of the mRNA whereas the 3' terminal sequence shown is followed by a poly (dA) tract 27 residues long, thus representing the complete sequence of the region. The predicted amino acid sequence is given below the nucleotide sequence and differences with the published amino acid sequence of mature ricin A and B chains (Funatsu G., Kimura, M and Funatsu, M. Agric. Biol. Chem. Vol 43, pp 2221–2224 (1979), and Yoshitake, S., Funatsu, G and Funatsu, M—Agric. Biol. Chem. Vol. 42, pp 1267–1274 (1978)) are indicated underneath. Residues absent from the published amino acid sequence are underlined with a dashed line and the position of amino acids present in the published sequence but absent from the derived sequence presented here are indicated by an asterisk. The dashed line beneath the 12 amino acid sequence linking the C-terminus of the A chain and the N-terminus of the B chain is bracketed. Amino acids are numbered from the amino terminal residue of the mature A chain and the preceding residues are indicated by negative numbers. Potential sites for asparagine linked N-glycosylation are boxed and potential poly (A) signals are underlined. The insert of pRCL6 extends from nucleotide—102 to residue 1512 and the insert of pRCL17 extends from nucleotide 733 to residue 1782.

The intervening twelve triplets code for the linker amino acid sequence which is present in the precursor polypeptide and which is enzymatically removed in the cell to separate the A and B chains, which chains are joined by a disulphide bridge during the formation of the ricin molecule itself. This linker region as well as the presumptive amino terminal leader or signal sequence (amino acids −24 to −1) are not present in the sequences already published by Funatsu et al.

Preroricin is the whole polypeptide coded for by the aforesaid DNA insert, i.e. from amino acid −24 to amino acid 541. Proricin, which is obtained from preroricin in the organism by removal of the amino acid leader sequence, extends from amino acid 1 to amino acid 541.

The following nucleotide sequence is designated the nucleotide sequence of Table 1. The following amino acid sequence is designated as the amino acid sequence of Table 1.

TABLE 1

| | | | | | | | | | | | |
|---|---|---|---|---|---|---|---|---|---|---|---|
| -100 | | | | | | -50 | | | | | |
| 5'-AAACCGGGAG | GAAATACTAT | | TGTAATATGG | | | | | | | | |
| | | -1 | | | | | | | | | |
| GAT | AAC | AAC | TTC | CCC | AAA | CAA | TAC | CCA | ATT | TAT | ATG |
| Asp | Asn | Asn | Phe | Pro | Lys | Gln | Tyr | Pro | Ile | Tyr | Met |
| | -1 | | | | | | | | | | |

| TAT | GCA | GTG | ACA | TGG | CTT | TGT | TTT | GCC | ACC | TCA | GGG | TGG | TCT | TTC | ACA | TTA | GAG |
|---|---|---|---|---|---|---|---|---|---|---|---|---|---|---|---|---|---|
| Tyr | Ala | Val | Thr | Trp | Leu | Cys | Phe | Ala | Thr | Ser | Gly | Trp | Ser | Phe | Thr | Leu | Glu |
| | | | | | | | | | 50 | | -10 | | | | | | |

| GTT | CGC | GGT | TTA | ACA | CGT | TTA | ATA | AAC | TTT | ACC | ACA | GCG | GGT | GCC | CAA | AGC | TAC | CAA | ATC | AGA | GCT |
|---|---|---|---|---|---|---|---|---|---|---|---|---|---|---|---|---|---|---|---|---|---|
| Val | Arg | Gly | Leu | Thr | Arg | Leu | Ile | Asn | Phe | Thr | Thr | Ala | Gly | Ala | Gln | Ser | Tyr | Gln | Ile | Arg | Ala |
| | 30 | | | | | | | Asn | Phe | Thr | | | | | | 20 | | | | | |
| | | | | | | | | 10 | | | | | | | | | | | | | |
| | | | | | | | | | | | | | | | | | | 150 | | | |

| ATT | TTA | GTT | GAA | CTC | TAT | GGA | GCT | ACT | GTG | AGA | CAT | CCA | GAT | ATA | CCA | GTT | GGT | TTT |
|---|---|---|---|---|---|---|---|---|---|---|---|---|---|---|---|---|---|---|
| Ile | Leu | Val | Glu | Leu | Tyr | Gly | Ala | Thr | Val | Arg | His | Pro | Asp | Ile | Pro | Val | Gly | Gly |
| | 60 | | | | | | | | | 40 | | Asp | Glu | | | | 50 | |
| | | | | | | | | | | | | Ser | | | | | | |

| AAT | AGC | GCA | TAT | TTC | TCA | AAT | CAT | CCT | CCA | GAT | GTT | ACT | TTA | ACA | TTA | GCA | GCA | ATA | AAC | TAC | GGA |
|---|---|---|---|---|---|---|---|---|---|---|---|---|---|---|---|---|---|---|---|---|---|
| Asn | Ser | Ala | Tyr | Phe | Ser | Asn | His | Pro | Pro | Asp | Val | Thr | Leu | Thr | Leu | Ala | Ala | Ile | Asn | Tyr | Gly |
| | 90 | | | | Gln | | | | | | 70 | | | | | | | | | 80 | |

| GCC | TTT | GTT | GAA | CTC | TTT | TAT | AAT | TAT | CCT | CAT | GAA | GAC | CAG | CCA | CTT | ACT | TTC | AAT | GTC | GCC | TAC |
|---|---|---|---|---|---|---|---|---|---|---|---|---|---|---|---|---|---|---|---|---|---|
| Ala | Phe | Val | Glu | Leu | Phe | Tyr | Asn | Tyr | Pro | His | Glu | Asp | Gln | Pro | Leu | Thr | Phe | Asn | Val | Ala | Tyr |
| | | | | | | | | | | 100 | | | | | | | | | 110 | | |
| | | | | | | | | | 200 | | | | | | | | | | | | |

| ATC | TCA | GCG | CTT | TAT | TAT | TAT | GGT | GGC | ATG | GAA | GAC | AGA | CTT | ATC | CTG | AGA | GCT | ACT | ACT | TTT | ATA | CAA | ATC | GGT | CAA |
|---|---|---|---|---|---|---|---|---|---|---|---|---|---|---|---|---|---|---|---|---|---|---|---|---|---|
| Ile | Ser | Ala | Leu | Tyr | Tyr | Tyr | Gly | Gly | Met | Glu | Asp | Arg | Leu | Ile | Leu | Arg | Ala | Thr | Thr | Phe | Ile | Gln | Gly | Leu |
| | 150 | | | | | | | | | | | | | | | | 130 | | | Phe | Ile | | | 140 | |
| | | | | | | | | | | | | | | | 300 | | | | | | | | | | |

| GCA | GCG | TTT | CTT | TAT | TAT | TAT | CAA | TAT | CAG | ACT | GCT | CGT | GTT | AAT | GCT | CGG | CCA | CAA | GGT | ATC | TGC | ATG | CGA | TAC | TTC |
|---|---|---|---|---|---|---|---|---|---|---|---|---|---|---|---|---|---|---|---|---|---|---|---|---|---|
| Ala | Ala | Phe | Leu | Tyr | Tyr | Tyr | Gln | Tyr | Gln | Thr | Ala | Arg | Val | Asn | Ala | Arg | Pro | Gln | Gly | Ile | Cys | Met | Arg | Tyr | Phe |
| | 150 | | | | | | | | 160 | | | | | Asn | Ala | Arg | | | | 170 | | | | | |
| | | | | | | | | | | | | | | | | | | | | | | | | 500 | |

| GCA | AGA | TTC | TCA | TAT | TAT | GAA | GGA | GAG | ATT | AGG | ACT | ACT | TCC | AGA | TCT | GCA | CCA | AGG | CAA | ATT | GGT | GAT | CCT | GTA | TGA | CTT |
|---|---|---|---|---|---|---|---|---|---|---|---|---|---|---|---|---|---|---|---|---|---|---|---|---|---|---|
| Ala | Arg | Phe | Ser | Tyr | Tyr | Glu | Gly | Glu | Ile | Arg | Thr | Thr | Ser | Arg | Ser | Ala | Pro | Arg | Gln | Gly | Asp | Pro | Val | Ser | Leu |
| | 180 | | | | | | | | | | | 190 | | | | | | | 200 | | | | | | |
| | | | | | | | 550 | | | | | | | | | | | | | | | 600 | | | | |

| GCA | GCA | AGA | TTC | CAA | TAT | ACG | AGA | ATT | TAC | AAC | CGG | AGG | TCT | GCA | AGC | ATT | GAA | ACA | ATT | ACA | CTT |
|---|---|---|---|---|---|---|---|---|---|---|---|---|---|---|---|---|---|---|---|---|---|
| Ala | Ala | Arg | Phe | Gln | Tyr | Thr | Arg | Ile | Tyr | Asn | Arg | Arg | Ser | Ala | Ser | Ile | Glu | Thr | Ile | Thr | Leu |
| | | | | | | | | | | | | | | | | | | | | | |

650                                                                                                                                                                                         700

TABLE 1-continued

| | | | | | | | | | | | | | |
|---|---|---|---|---|---|---|---|---|---|---|---|---|---|
| GAG | AAT | AGT | TGG | GGG | AGA | CTT | TCC | ACT | GCA | ATT | CAA | AAC | CAA | AGA | CGT | AAT | GGT |
| Glu | Asn | Ser | Trp | Gly | Arg | Leu | Ser | Thr | Ala | Ile | Gln | Asn | Gln | Arg | Arg | Asn | Gly |
| | 210 | | | | | | | | | | 220 | | | | | | Asp |
| | | | | | | | | | | | | | | | | | 800 |

TCC AAA TTC AGT TAC GAT GTG ATA TTA ATC CCT GAG TCT ATA GCT CTC ATG GTG TAT AGA TGC GCA CCT CCA ATT GCC TTT
Ser Lys Phe Ser Tyr Asp Val Ile Leu Ile Pro Ser Ile Ala Leu Met Val Tyr Arg Cys Ala Pro Pro Ile Ala Phe
240 250 Leu 260

TCT TGT CTT GTG AGG CCA GTA GTG AAT GCT GAT GTT TGT ATA CAG ATG GAT CCT GGT
Ser Cys Leu Val Arg Pro Val Val Asn Ala Asp Val Cys Ile Gln Met Asp Pro Gly
(---) — — — — — — — — 280 — — — — — — — —

TCT ACT TTG GAT GTT GAT ATT AAC TTT CAC AGA AGA TTC AGA GGA AGG AAC GCA AAG TGT GGA CAG ATA TTA CAG CCC GGA TAC TCT CCT GTA
Ser Thr Leu Asp Val Asp Ile Asn Phe His Arg Arg Phe Arg Gly Arg Asn Ala Lys Cys Gly Gln Ile Leu Gln Pro Gly Tyr Ser Pro Val
300 310 320 950

CTA TGT GAT AGG AGA AGA AAA AGA GCT ACT AAT GAC ACT CAG TGC CGA ACT ATT TTA ACT TAC TGG GGG CGT AAT ATC
Leu Cys Asp Arg Arg Arg Lys Arg Ala Thr Asn Asp Thr Gln Cys Arg Thr Ile Leu Thr Tyr Trp Gly Arg Asn Ile
330 340 Asp 1000 1050

TGG TGT AAT ACT GCT GAT GAT GCA ACC ACG TGG CGC TGG AAC GTA CCG GGA TCT CCA
Trp Cys Asn Thr Ala Asp Asp Ala Thr Thr Trp Arg Trp Asn Val Pro Gly Ser Pro
360 380

GAT TGC ACA GGG AAC ACT ACC ACA ACA CTT TAT CTT GAT TGG AAC AAC ATT AAT AAT ACA GAA AAG CAA
Asp Cys Thr Gly Asn Thr Thr Thr Thr Leu Tyr Leu Asp Trp Asn Asn Ile Asn Asn Thr Glu Lys Gln
390 400

GCG ACA TCA GTT ACA ACC ATT GCA TGT GTT CAG TGG CAA GTA CAA GGA GTC GTT ATG GTA TCT GAG GAC AGT GAA AAG
Ala Thr Ser Val Thr Thr Ile Ala Cys Val Gln Trp Gln Val Gln Gly Val Val Met Val Ser Glu Asp Ser Glu Lys
420 Val 1200 1250

CCT TTT ACT TGC TGC CTA TAT TAT GGT CAA GCA AAT AGT GGA CGA GAC ATA GTT TTA ATA CGG
Pro Phe Thr Cys Cys Leu Tyr Tyr Gly Gln Ala Asn Ser Gly Arg Asp Ile Val Leu Ile Arg
Trp 430 440 1300

CCT GAA CAA CAG TGG CTT GCT TAT CGT CAA GAT AAT AAC CAA AAC GTA AAT AAT GAT ATA CGG
Pro Glu Gln Gln Trp Leu Ala Tyr Arg Gln Asp Asn Asn Gln Asn Val Asn Asn Asp Ile Arg
1350 1400

TABLE 1-continued

```
Ala Glu Gln Gln Trp Ala Leu Tyr Ala Asp Gly Ser Ile Arg Pro Gln Gln Asn Arg Asp Asn Cys Leu Thr Ser Asp Ser Asn Ile Arg
                                             Asn     Asn       Arg
GAA ACA GTT AGG ATC CTC TCT TGT GGC CCT TCC GCA TCT CGA TGG ATG TTC AAC AAT GAT GGA ACC ATT TTA AAT TTG TAT
Glu Thr Val Lys Ile Leu Ser Cys Gly Pro Ser Ala Ser Arg Trp Met Phe Asn Asn Asp Gly Thr Ile Leu Asn Leu Tyr
    480                                      490         Glu                        500                    1600
AGT GGA TTG GTG TTA GAT GTG ACG CGA GAT CCG AGC CTT AAA CAA ATC ATT CTT TAC CCT CTC CAT GGT GAC CCA AAC CAA ATA TGG
Ser Gly Leu Val Leu Asp Val Thr Arg Asp Pro Ser Leu Lys Gln Ile Ile Leu Tyr Pro Leu His Gly Asp Pro Asn Gln Ile Trp
510                     Arg                 520                                         Trp    *                    ---
                        Ala
TTA CCA TTA TTT TGA TAGACAGATT ACTCTCTTGC AGTGTGTGTG TCCTGCCATG AAAATAGATG GCTTAAATAA AAAGGACATT GTAAATTTTG TAACTGAAAG
Leu Pro Leu Phe ***
*Leu Pro                                     1650                                           1700
GACAGCAAGT TATTGCAGTC CAGTATCTAA TAAGAGCACA ACTATTGTCT TGTGCATTCT AAATTTT-Poly(A)
                      1750                                   1780
```

We claim:

1. A biologically pure sample of a DNA molecule, said DNA molecule comprising at least a substantial portion of:
   (a) nucleotides 1–801 of the nucleotide sequence shown in Table 1, or
   (b) a nucleotide sequence that is equivalent by virtue of degeneracy of the genetic code to nucleotides 1–801 of the nucleotide sequence shown in Table 1,
wherein said portion encodes a polypeptide which inhibits protein synthesis at 60S subunits of ribosomes.

2. A method of producing a polypeptide having a biological activity of ricin, comprising: synthesizing a polypeptide consisting of amino acids −24 to 541 of the amino acid sequence shown in Table 1.

3. A method of producing a polypeptide having a biological activity of ricin, comprising: synthesizing a polypeptide consisting of amino acids 1–541 of the amino acid sequence shown in Table 1.

4. A method of producing a polypeptide having a biological activity of ricin, comprising: translating an mRNA molecule which is the mRNA equivalent of nucleotides –72 to 1626 of the DNA sequence shown in Table 1.

5. A method of producing a polypeptide having a biological activity of ricin, comprising: translating an mRNA molecule which is the mRNA equivalent of nucleotides 1 to 1626 of the DNA shown in Table 1.

6. A method of producing a polypeptide having a biological activity of ricin, comprising: translating an mRNA molecule which is the mRNA equivalent of nucleotides 1 to 801 of the DNA shown in Table 1.

7. The method of claim 4 wherein said translating is in vitro.

8. The method of claim 5 wherein said translating is in vitro.

9. The method of claim 6 wherein said translating is in vitro.

10. The method of claim 7 wherein said translating is in a reticulocyte lysate cell free system.

11. The method of claim 8 wherein said translating is in a reticulocyte lysate cell free system.

12. The method of claim 9 wherein said translating is in a reticulocyte lysate cell free system.

13. The biologically pure sample of claim 1 wherein the DNA molecule comprises nucleotides 1–801 of the nucleotide sequence shown in Table 1.

14. The biologically pure sample of claim 1 wherein the DNA molecule comprises a sequence which is equivalent to nucleotides 1–801 of the nucleotide sequence shown in Table 1 by virtue of degeneracy of the genetic code.

15. A host cell comprising the DNA molecule of claim 1.

* * * * *